(12) United States Patent
Letton et al.

(10) Patent No.: US 6,209,388 B1
(45) Date of Patent: Apr. 3, 2001

(54) ULTRASONIC 2-PHASE FLOW APPARATUS AND METHOD

(75) Inventors: Winsor Letton; Klaus J. Zanker, both of Houston, TX (US)

(73) Assignee: Daniel Industries, Inc.

( * ) Notice: Subject to any disclaimer, the term of this patent is extended or adjusted under 35 U.S.C. 154(b) by 0 days.

(21) Appl. No.: 09/146,085

(22) Filed: Sep. 2, 1998

Related U.S. Application Data

(63) Continuation-in-part of application No. 08/613,478, filed on Mar. 11, 1996.

(51) Int. Cl.⁷ ............................ G01N 29/02; G01N 29/20
(52) U.S. Cl. .................. 73/61.79; 73/861.04; 73/861.28
(58) Field of Search .............................. 73/19.03, 19.04, 73/24.01, 24.04, 29.01, 61.45, 61.79, 861.04, 861.18, 861.28

(56) References Cited

U.S. PATENT DOCUMENTS

| | | | |
|---|---|---|---|
| H608 | * | 3/1989 | Goolsby ............................ 73/861.25 |
| 3,623,363 | * | 11/1971 | Dory ................................... 73/61.45 |
| 4,138,879 | | 2/1979 | Liebermann . |
| 5,415,048 | * | 5/1995 | Diatschenko et al. ............ 73/861.04 |
| 5,600,073 | * | 2/1997 | Hill ................................... 73/861.04 |
| 5,714,691 | | 2/1998 | Hill . |
| 5,719,329 | * | 2/1998 | Jepson et al. ..................... 73/861.04 |
| 5,792,962 | * | 8/1998 | Constant et al. .................. 73/861.04 |
| 5,861,755 | * | 1/1999 | Moerk et al. ..................... 73/861.04 |

FOREIGN PATENT DOCUMENTS

| | | | |
|---|---|---|---|
| 0691527 | 1/1996 | (EP) | ................................. 73/861.04 |
| 14382 | 7/1993 | (WO) | ................................ 73/861.04 |

* cited by examiner

*Primary Examiner*—Daniel S. Larkin
(74) *Attorney, Agent, or Firm*—Conley, Rose & Tayon, P.C.

(57) ABSTRACT

An apparatus and related method for measuring the properties and individual flow rates of a two-phase flow comprising a gas and a liquid is disclosed. This apparatus and related method also can determine whether the liquid is travelling in primarily a mist or stratified flow. More precisely, one embodiment of the disclosed invention uses measured parameters such as gain, standard deviation in upstream and downstream travel times for an ultrasonic signal, measured speed of sound, noise, signal quality, batch failure rate, and velocity profile to infer the amount of liquid in the gas flow, and in what form the liquid is travelling. For a horizontal two-phase flow, an internal measurement can be used as a dry gas reference, although the invention is also applicable to a vertical flow. For increased confidence, these determinations may be corroborated by the disclosed liquid level measurement device.

20 Claims, 12 Drawing Sheets

ULTRASONIC 2-PHASE FLOW APPARATUS AND METHOD

CROSS-REFERENCE TO RELATED APPLICATIONS

This is a continuation-in-part of and claims benefit to now pending Ser. No. 08/613,478 filed Mar. 11, 1996.

STATEMENT REGARDING FEDERALLY SPONSORED RESEARCH OR DEVELOPMENT

Not Applicable.

BACKGROUND OF THE INVENTION

1. Field of the Invention

A disclosed embodiment of the invention relates generally to the detection of two-phase flow. More particularly, a disclosed embodiment of the invention relates to the detection of liquid in a gas stream by an ultrasonic meter. Even more particularly, a disclosed embodiment of the invention relates to the measurement by an ultrasonic meter of the amount and form of flow for a liquid travelling through a pipeline and the properties of the accompanying gas stream.

2. Description of the Related Art

After a hydrocarbon such as natural gas has been removed from the ground, it is commonly transported from place to place via pipelines. Often this gas stream also contains a certain amount, or percent fraction, of liquid. As is appreciated by those of skill in the art, it is desirable to know with accuracy the amount of gas in the gas stream. It is also extremely desirable to know how much liquid is being transported along with the gas stream. For example, if the gas contains "natural gas liquids" or condensates, a seller of gas wants extra compensation for this energy-rich liquid. Thus, particular accuracy for gas flow and liquid fraction measurements is demanded when gas (and any accompanying liquid) is changing hands, or "custody."

Gas flow meters have been developed to determine how much gas is flowing through the pipeline. One type of meter to measure gas flow is called an ultrasonic flow meter. Ultrasonic flow meters, also named sonic or acoustic flow meters, are revolutionizing the gas industry because of their many advantages.

FIG. 1A shows an ultrasonic meter suitable for measuring gas flow. Spoolpiece 100, suitable for placement between sections of gas pipeline, has a predetermined size and thus defines a measurement section. A pair of transducers 120 and 130, and their respective housings 125 and 135, are located along the length of spoolpiece 100. A path 110, sometimes referred to as a "chord" exists between transducers 120 and 130 at an angle θ to a centerline 105. The position of transducers 120 and 130 may be defined by this angle, or may be defined by a first length L measured between transducers 120 and 130, a second length X corresponding to the axial distance between points 140 and 145, and a third length D corresponding to the pipe diameter. Distances X and L are precisely determined during meter fabrication. Points 140 and 145 define the locations where acoustic signals generated by transducers 120 and 130 enter and leave gas flowing through the spoolpiece 100 (i.e. the entrance to the spoolpiece bore). In most instances, meter transducers, such as 120 and 130, are placed a specific distance from points 140 and 145, respectively, regardless of meter size (i.e. spoolpiece size). A fluid, typically natural gas, flows in a direction 150 with a velocity profile 152. Velocity vectors 153–158 indicate that the gas velocity through spoolpiece 100 increases as centerline 105 of spoolpiece 100 is approached.

Transducers 120 and 130 are ultrasonic transceivers, meaning that they both generate and receive ultrasonic signals. "Ultrasonic" in this context refers to frequencies above about twenty kilohertz. Typically, these signals are generated and received by a piezoelectric element in each transducer. Initially, D transducer 120 generates an ultrasonic signal that is then received at, and detected by, U transducer 130. Some time later, U transducer 130 generates a reciprocal ultrasonic signal that is subsequently received at and detected by D transducer 120. Thus, U and D transducers 120 and 130 play "pitch and catch" with ultrasonic signals 115 along chordal path 110. During operation, this sequence may occur thousands of times per minute.

The transit time of the ultrasonic wave 115 between transducers U 130 and D 120 depends in part upon whether the ultrasonic signal 115 is traveling upstream or downstream with respect to the flowing gas. The transit time for an ultrasonic signal traveling downstream (i.e. in the same direction as the flow) is less than its transit time when traveling upstream (i.e. against the flow). The upstream and downstream transit times can be used to calculate the average velocity along the signal path. Given the cross-section measurements of the meter carrying the gas, the average velocity over the area of the gas may be used to find the quantity of gas flowing through spoolpiece 100. Alternately, a meter may be designed to attach to a pipeline section by, for example, hot tapping, so that the pipeline dimensions instead of spoolpiece dimensions are used to determine the average velocity of the flowing gas.

In addition, ultrasonic gas flow meters can have one or more paths. Single-path meters typically include a pair of transducers that project ultrasonic waves over a single path across the axis (i.e. center) of spoolpiece 100. In addition to the advantages provided by single-path ultrasonic meters, ultrasonic meters having more than one path have other advantages. These advantages make multi-path ultrasonic meters desirable for custody transfer applications where accuracy and reliability are crucial.

Referring now to FIG. 1B, a multi-path ultrasonic meter is shown. Spoolpiece 100 includes four chordal paths A, B, C, and D at varying levels through the gas flow. Each chordal path A–D corresponds to two transceivers behaving alternately as a transmitter and receiver. Also shown is an electronics module 160, which acquires and processes the data from the four chordal paths A–D. This arrangement is described in U.S. Pat. No. 4,646,575, the teachings of which are hereby incorporated by reference. Hidden from view in FIG. 1B are the four pairs of transducers that correspond to chordal paths A–D.

The precise arrangement of the four pairs of transducers may be more easily understood by reference to FIG. 1C. Four pairs of transducer ports are mounted on spoolpiece 100. Each of these pairs of transducer ports corresponds to a single chordal path of FIG. 1B. A first pair of transducer ports 125 and 135 including transducers 120 and 130 is mounted at a non-perpendicular angle θ to centerline 105 of spoolpiece 100. Another pair of transducer ports 165 and 175 including associated transducers is mounted so that its chordal path loosely forms an "X" with respect to the chordal path of transducer ports 125 and 135. Similarly, transducer ports 185 and 195 are placed parallel to transducer ports 165 and 175 but at a different "level" (ie. a different radial position in the pipe or meter spoolpiece). Not explicitly shown in FIG. 1C is a fourth pair of transducers and transducer ports. Taking FIGS. 1B and 1C together, the pairs of transducers are arranged such that the upper two pairs of transducers corresponding to chords A and B form an X and the lower two pairs of transducers corresponding to chords C and D also form an X.

Referring now to FIG. 1B, the flow velocity of the gas may be determined at each chord A–D to obtain chordal flow velocities. To obtain an average flow velocity over the entire pipe, the chordal flow velocities are multiplied by a set of predetermined constants. Such constants are well known and were determined theoretically.

This four-path configuration has been found to be highly accurate and cost effective. Nonetheless, other ultrasonic meter designs are known. For example, other ultrasonic meters employ reflective chordal paths, also known as "bounce" paths. Referring now to FIG. 18, a spoolpiece or pipeline 1800 includes ultrasonic paths 1810 and 1820 representing two travel paths of generated ultrasonic signals. A first ultrasonic signal originates at a first transducer along the circumference of the spoolpiece and follows path 1810. After generation, this first ultrasonic signal travels through the center 1830 of the spoolpiece before reflecting off an opposite wall 1840 of the spoolpiece. It then once again travels through the center 1830 of the spoolpiece before being received at a second transducer. A second ultrasonic signal originates at a third transducer along the circumference of the spoolpiece, reflects a first time off an opposite wall 1850 of the spoolpiece, reflects a second time off a different opposite wall 1860 of the spoolpiece, and then is received at a fourth transducer. As contrasted to ultrasonic path 1810, ultrasonic path 1820 does not travel through center 1830. Each of these signal paths 1810, 1820 include ultrasonic signals travelling both upstream and downstream.

Another bounce path ultrasonic meter design is shown in FIG. 19. A spoolpiece or pipeline 1900 includes a non-bounce path 1910 travelling through the center 1930 of the spoolpiece 1900 and a bounce path 1920. Bounce path 1920 reflects off wall 1940. These bounce path designs are exemplary only, and other bounce path designs are also known.

A pipeline may carry liquid in addition to the gas stream. The liquid generally travels through the pipeline in one of two forms. In particular, a "mist flow" of liquid in the pipeline consists of small droplets spread out in the gas flow. These small droplets of liquid are buoyed by and carried along with the turbulence of the moving gas. Thus, liquid traveling in mist form through the pipeline is carried along at approximately the same speed as the gas. A "stratified flow" of liquid consists of a stream or river traveling along one area of the pipeline, such as the bottom. This stream of liquid typically travels at a different rate than that of the gas moving above it. Because the determination of a liquid flow by a pipeline depends not only upon the percent volume the liquid occupies but also upon its velocity, it is helpful to know the form in which the liquid is travelling.

Therefore, a meter is needed that is capable of measuring the amount of fluid in a gas stream. Ideally, this meter's volume fraction measurements would not be susceptible to the high error associated with the teachings of the prior art. Further, such an ideal meter would provide a reliable indication of the nature of the liquid in the pipeline. It would also be desirable if this meter could be used with only minimal changes to prior art gas flow meters. Ideally, this meter would also solve many other problems present in the prior art.

SUMMARY OF THE INVENTION

Disclosed embodiments of the invention feature use of a plurality of measurements that are suitable for determining the properties and individual flow rates of a two-phase flow through a pipe. More precisely, one embodiment of the disclosed invention uses measured parameters, such as gain, standard deviation in upstream and downstream travel times for an ultrasonic signal, measured speed of sound, calibration error, noise, signal quality, batch failure rate, and velocity profile, to infer the amount of liquid in the gas flow, and in what form the liquid is travelling. Another embodiment also uses an ultrasonic transducer to directly measure the liquid level in the meter or pipeline.

The present invention comprises a combination of features and advantages that enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figure 2:
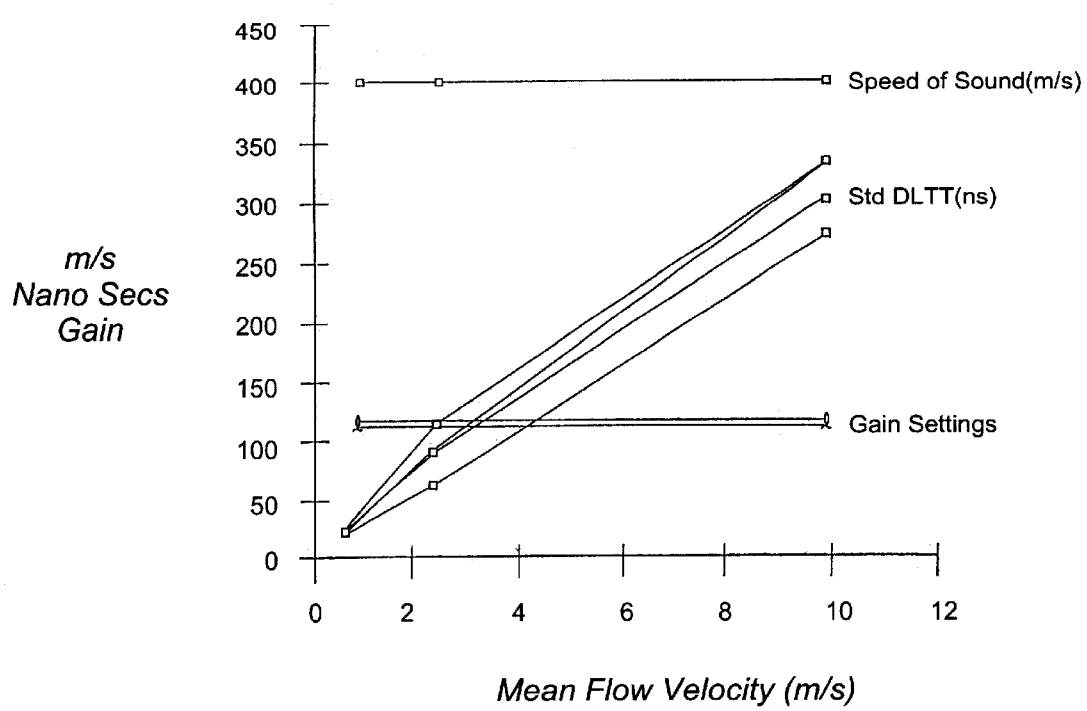
FIG. 2 is a graph illustrating the parameters of a dry gas stream.

FIG. 2 is a graph illustrating certain parameters measured by an ultrasonic flow meter in a dry gas stream at varying mean flow velocities. In particular, FIG. 2 shows a mean flow velocity—speed of sound relationship, a mean flow velocity—standard deviation (Std DLTT) relationship for the differences in upstream and downstream travel times, and a mean flow velocity—gain relationship. The X-axis has a range of 0 to 12 meters/second, and the Y-axis has a range of 0 to 450 of various units, as shown. The mean flow velocity represents the average speed of the gas flowing through a meter. The speed of sound measurement represents the speed of sound for a particular gas flowing through the meter. "Standard deviation" is a mathematical term denoting a measure of the dispersion or variation in a distribution, equal to the square root of the arithmetic mean of the squares of the deviations from the arithmetic mean. Hence, changes in the standard deviation for the differences in upstream and downstream travel times is an indication of the variability in ultrasonic signal travel times. The gain, also called amplifier gain, is a measure of the amount of attenuation or weakening of a transmitted ultrasonic signal. More particularly, as an ultrasonic signal travels across a spoolpiece, it naturally attenuates (ie. weakens). Upon being received, an amplifier amplifies the received signal to a desired and predetermined strength. Where for some reason the attenuation of the transmitted ultrasonic signal is unusually great, and thus the signal is weak, the amplifier must boost or amplify it more to obtain the desired and predetermined strength. The amount of this amplification is measured by the parameter known as gain.

As can be seen, in a dry gas stream the gain measurement and the speed of sound measurement are constant. However, the standard deviation of the travel time difference increases in a linear fashion with an increased mean flow velocity. The illustrated relationships are shown for a 150 millimeter (mm) meter and are expected to change with meters of different sizes.

Figure 3:
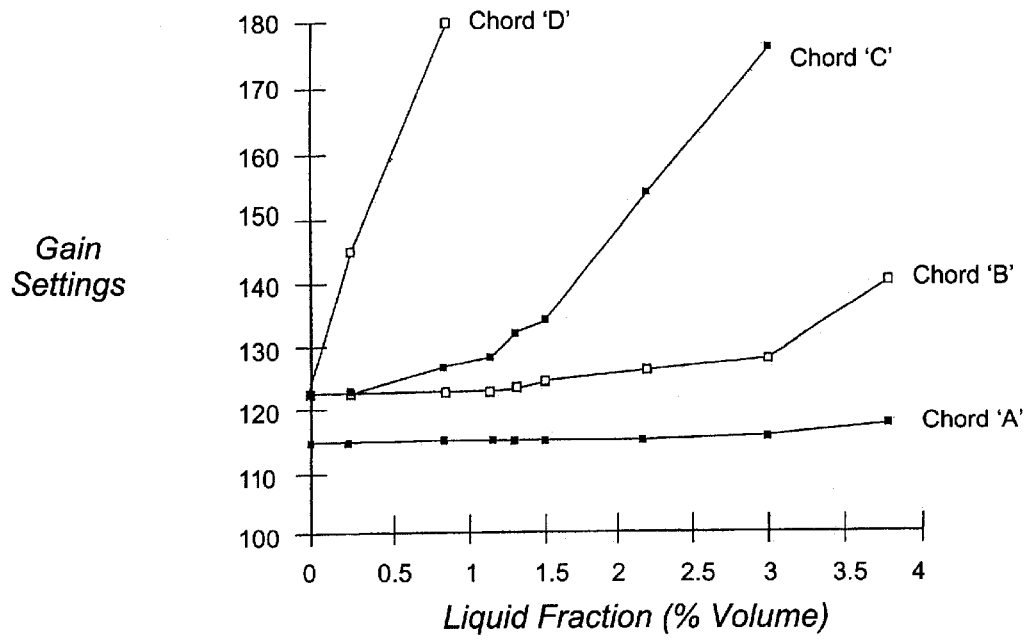
FIG. 3 is a graph illustrating a percent liquid fraction—gain relationship.

FIG. 3 is a graph of a percent liquid fraction—gain relationship for a horizontal or near 18 horizontal ultrasonic flow meter. Along the X-axis is a range of percent liquid from 0% to 4%. Along the Y-axis, a range of gain settings from 100 to 180 is shown. The gain is shown for each chord A–D. As can be seen, the attenuation along chord D is most severe. The attenuation along chord C is the next highest, the attenuation along chord B is less severe than along chord C, and the attenuation along chord A is least severe of all.

Figure 1A:
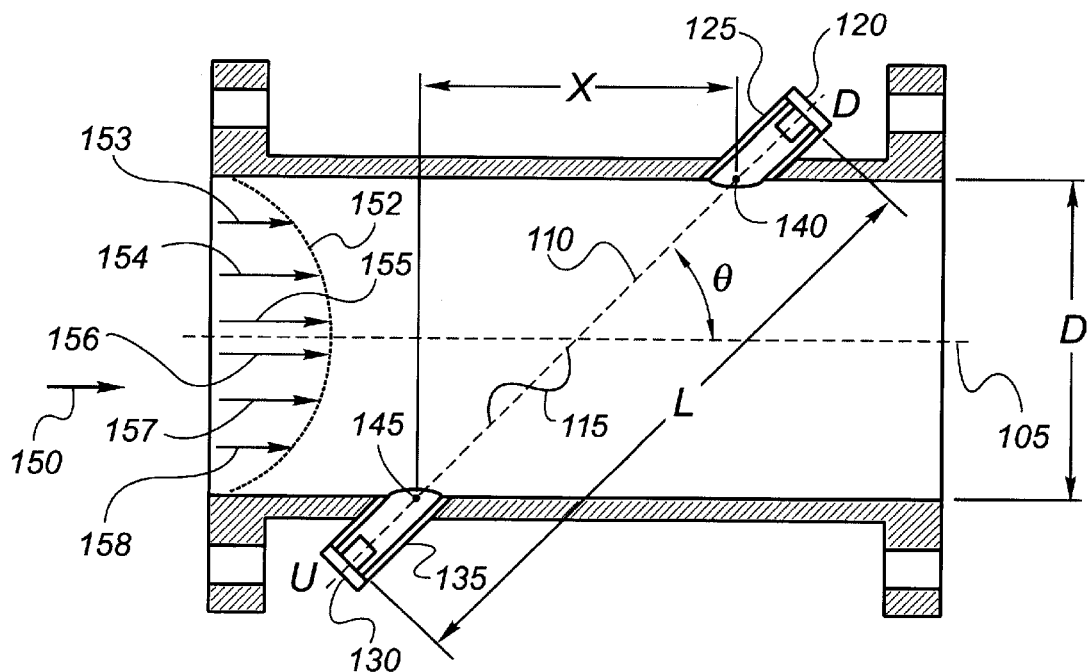
FIG. 1A is a cut-away top view of an ultrasonic gas flow meter.
Figure 1B:
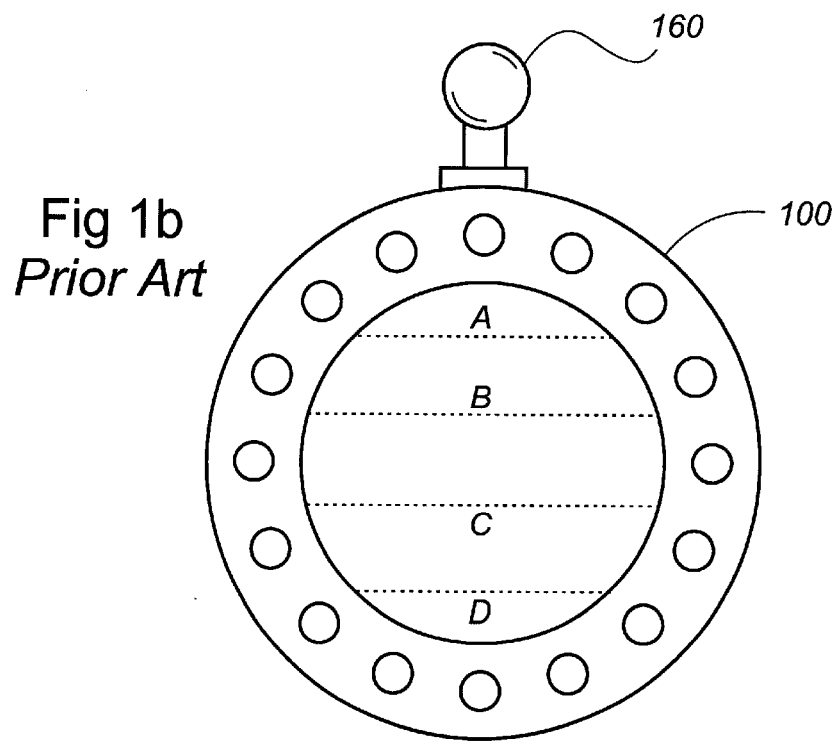
FIG. 1B is an end view of a spoolpiece including chordal paths A–D.

The phenomenon can be explained by gravity. Where liquid is traveling through a pipeline in a mist flow, it could be expected that in a gravity-free environment it would occupy the entire pipeline. However, in actual operation in a horizontal or near-horizontal pipe, it might also be expected that gravity would affect the droplets of liquid that make up the mist flow, such that the mist would be more dense toward the bottom of the pipleline and less dense toward the top. As used herein, the term "near-horizontal" denotes any angle at which gravity affects the mist flow in this manner, including horizontal. Thus, the mixture of gas and liquid travelling along the top of the associated meter in a mist flow would have significantly less fluid than would the mixture at the bottom. As illustrated in FIG. 1B, chords A–D are arranged from the top of a spoolpiece to the bottom, so that chord D travels through a much denser mist than does chord A. As such, chord A (or more broadly any chord that travels primarily through an upper portion of a spoolpiece) approximates dry gas conditions. Thus, the gravity-induced distribution of a mist flow may be advantageous to the practitioner who desires a dry gas reference inside the meter and additional confirmation of mist flow. The resulting gradient across the chords may also be used to confirm mist flow. It should be noted that if gravity (or other force) does not affect the mist flow in this manner, e.g., vertical flow, and there is no dry gas reference inside the meter, the diagnostics disclosed herein can still detect percent liquid fraction and flow rates.

Therefore, the gain measurements of FIG. 3 provide an indication of the amount of fluid in a gas stream. Nonetheless, certain drawbacks exist to using gain as an indicator of the amount of fluid in a gas stream. As can be appreciated by those of skill in the art, in addition to the increased weakening of a signal as it travels through a "wet" gas stream, gain measurements may change because of other phenomena. For example, gain measurements may change because of transducer failure. As another example, where a liquid mist is originally present in the gas flow, it may cause the accrual of a foreign substance on the face of transmitting and receiving transducers. Such a coating on the transducer face could interfere with ultrasonic signals and increase amplifier gain (and thus suggest that fluid is present in the gas flow, even when it is not). Indeed, such a phenomenon would be consistent with the chord-by-chord gain pattern described above.

Figure 4:
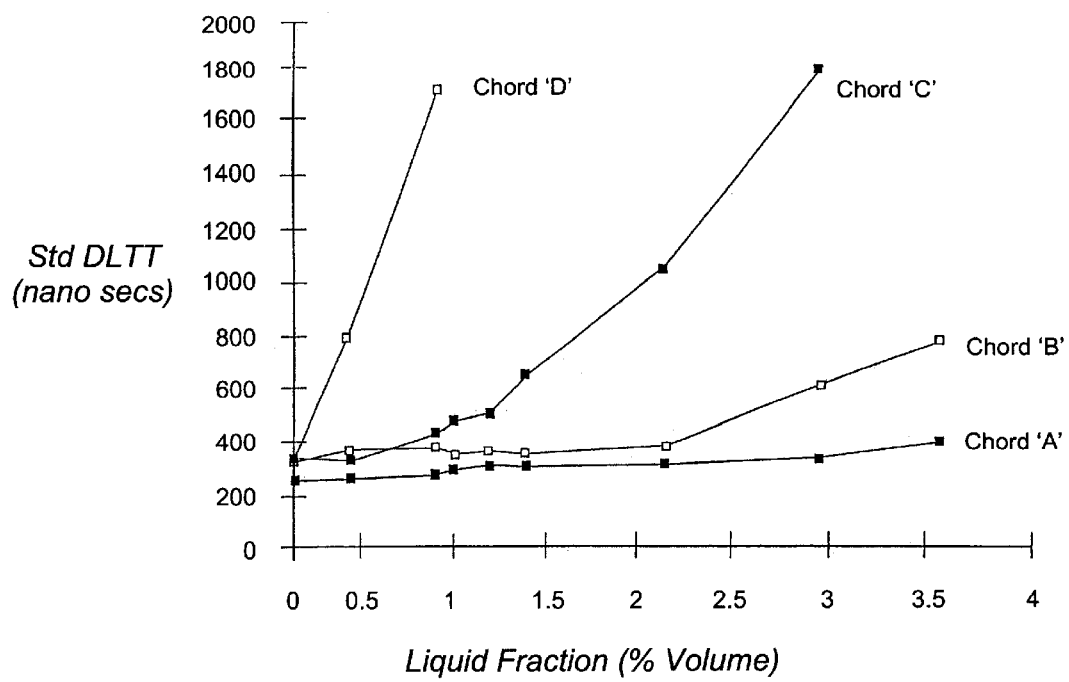
FIG. 4 is a graph illustrating a percent liquid fraction—standard deviation relationship

FIG. 4 is a graph of a percent liquid fraction—standard deviation relationship for the difference of upstream and downstream travel times. The X-axis spans a range of percent liquid from 0% to 4%. The Y-axis includes a range of nanoseconds from 0 to 2000. Data for each chord A–D is shown. As can be seen, as the fluid fraction goes up, the standard deviation of the travel time difference $\Delta t$ generally increases. In particular, the increase is greatest at the bottom of the meter near chords C and D, and is less pronounced near the top of the meter at chords A and B.

This effect and distribution can be explained by liquid droplet interference to an ultrasonic signal. Such interference would be affected by the density of the mist, but would not depend on whether the ultrasonic signal is travelling upstream or downstream. Thus, gravity once again explains why the effect is most severe on the lowermost chord.

Nonetheless, although the standard deviation of the difference in travel times increases as percent liquid fraction increases, an increase in percent liquid fraction is not the only explanation for an increased standard deviation in travel times. For example, the standard deviation of the difference in transit times may increase because of noise in the pipeline. Such increased standard deviations may also be due to upstream or downstream pulsations in the gas flow, such as made by pipe fittings or compressors. Thus, the sole use of Std DLTT is not a reliable indicator of percent liquid fraction by volume.

Figure 5:
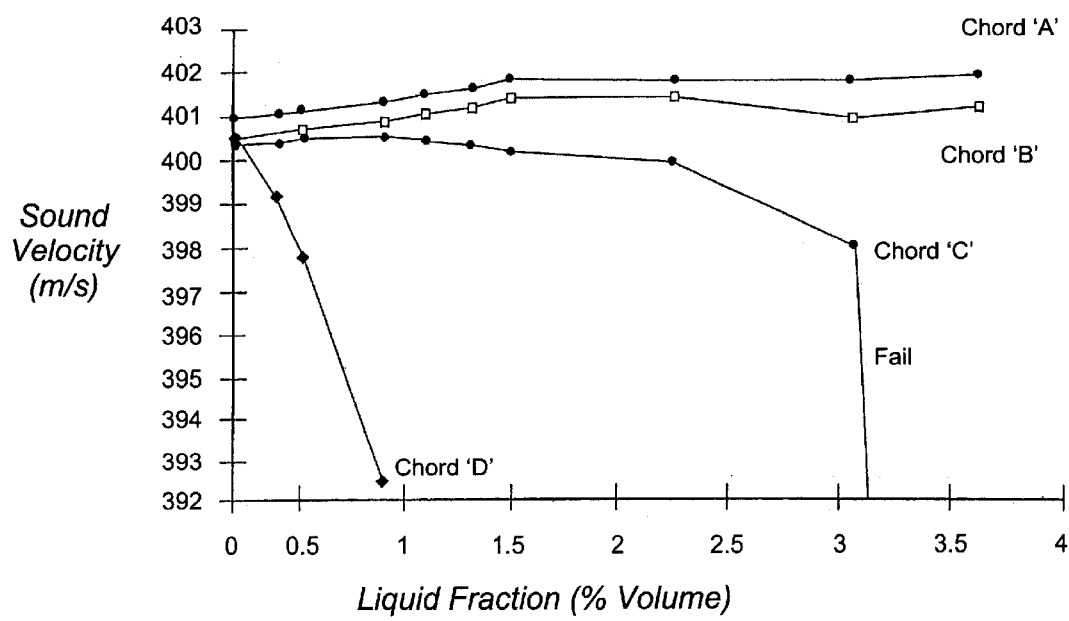
FIG. 5 is a first graph illustrating a liquid fraction—measured speed of sound relationship.

FIG. 5 is a graph of a liquid fraction—measured speed of sound relationship. It could be expected that a speed of sound measurement would be affected by fluid in the gas flow because the speed of sound measurement is based upon the measured travel times. Further, the effects of gravity suggest that lower chord speed of sound measurements would be affected more than upper chord speed of sound measurements. As can be seen, upper chords A and B are generally unaffected at flow velocities up to ten meters per second with liquid fractions below about 4%. However, lower chords C and D show a drop-off in the measured speed of sound as fluid is introduced into the gas stream. For chord D, this drop off begins almost immediately upon introduction of a fluid mist into the gas stream. For chord C, this effect begins at around 2% liquid fraction. However, it should be noted that the flow velocity shown is ten meters per second and the maximum change of the velocity of sound was approximately eight meters per second, or 2%. This change in speed of sound may be hard to distinguish from the typical errors present in making a speed of sound measurement.

In addition, other explanations also exist for variations in speed of sound measurements. For example, variations in the measured speed of sound could be caused by a change in the gas pressure in the pipeline, or by a temperature change in the pipeline. Such variations in the speed of sound measurement could alternately be caused by a variation in the composition of the gas, or by problems with a transducer, or by some combination of the above.

Figure 6:
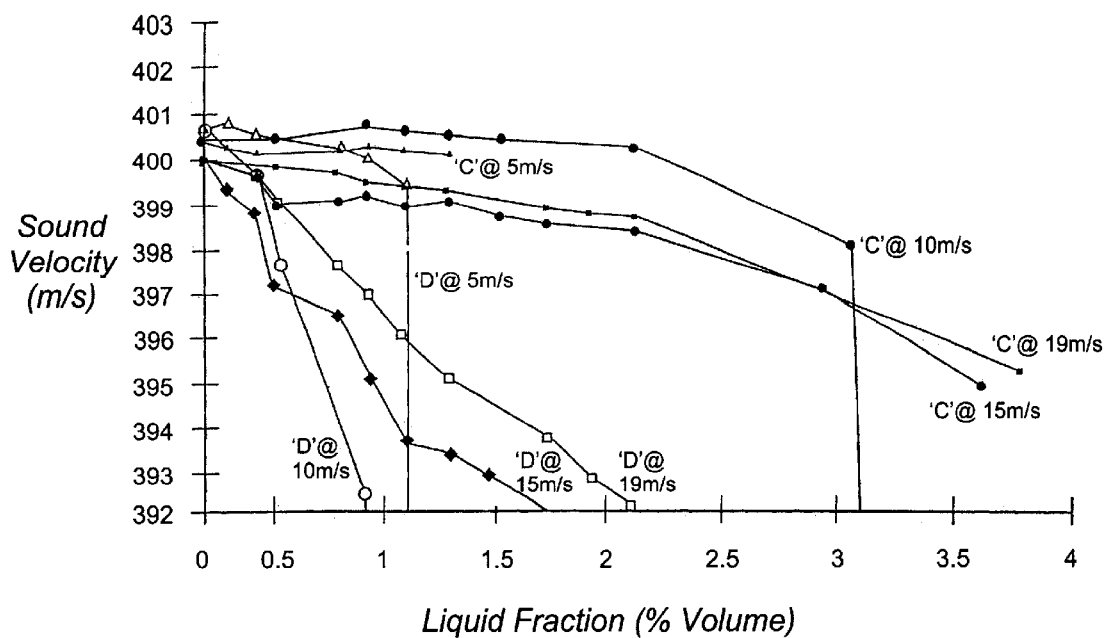
FIG. 6 is a second graph illustrating a liquid fraction—measured speed of sound relationship.

FIG. 6 is similar to FIG. 5, but shows the effect of varying liquid fraction on speed of sound measurements for a variety of flow velocities. To simplify presentation, only chords C and D are shown. One explanation for the disparity between the curves measured at flows of approximately five meters per second and those of higher flows is that above gas flows of about five meters per second, it is expected that a stratified flow of fluid will begin to acquire mist flow characteristics. More particularly, the fluid may move through a series of forms, from stratified flow to annular flow to annular mist to mist. These changes will be due to the turbulent gas flow above the stratified flow entraining (i.e. siphoning off) and carrying with it droplets from the surface of the stratified flow.

Certain of the inventor's findings regarding speed of sound, transit time, and gain measurements as criteria to estimate Liquid Volume Fraction in a gas stream were presented in U.S. patent application Ser. No. 08/613,478 "Ultrasonic Fraction and Flow Apparatus and Method," the contents of which are hereby incorporated by reference.

Figure 7:
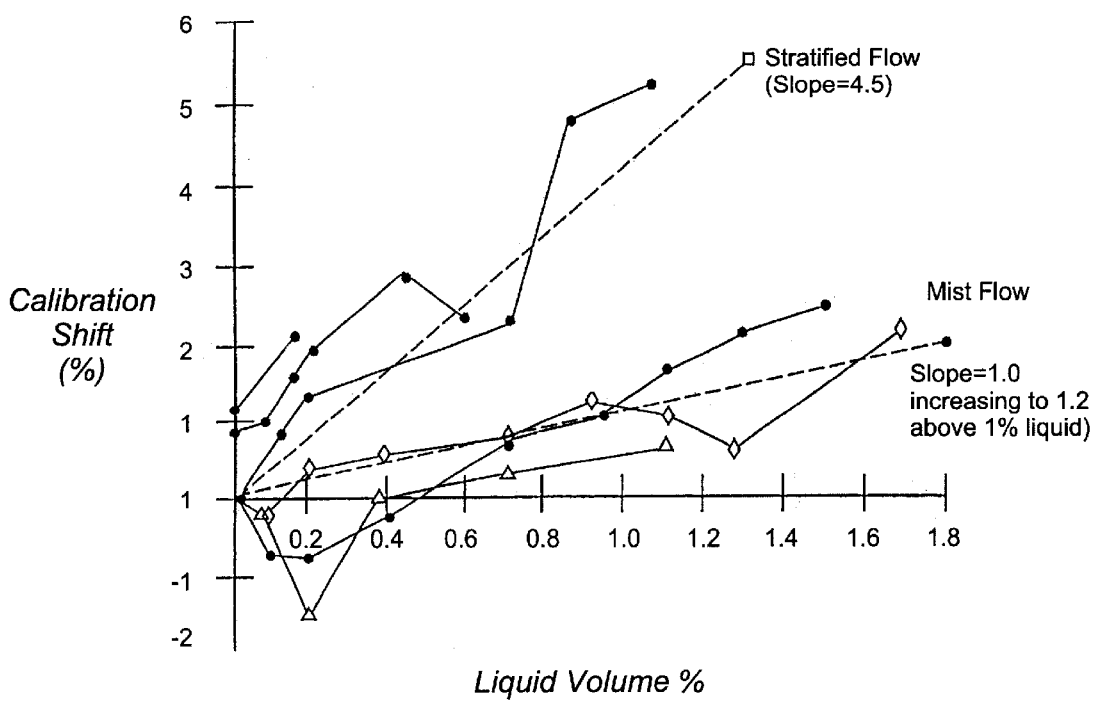
FIG. 7 is a graph illustrating a liquid fraction—calibration error relationship.

FIG. 7 is a graph of a liquid volume—calibration error relationship for a wet gas stream in an ultrasonic flow meter. As can be seen, the data shows a marked distinction between stratified flow and mist flow with respect to calibration shift. For stratified flow, every one percent of liquid volume causes an increase in gas measurement error of about 4.5%. For mist flow, each one percent increase in liquid volume results in approximately a 1% error in calibration shift.

However, error in calibration is not known in practice and thus an accurate measure of calibration error typically requires the use of another monitoring device (such as at a calibration facility). As such, it is not an ideal, or even practical, criterion to determine the amount and properties of liquid in a gas flow.

Countless other parameters exist whose measurement is possible by an ultrasonic flow meter, but whose relevance to determining the characteristics of a two-phase flow was previously unknown. Among these, an analysis of the noise in an ultrasonic meter may be indicative of the amount of fluid in the gas stream. More precisely, an increased amount of noise arriving before the signal indicates that fluid may be present in the gas flow.

Figure 8:
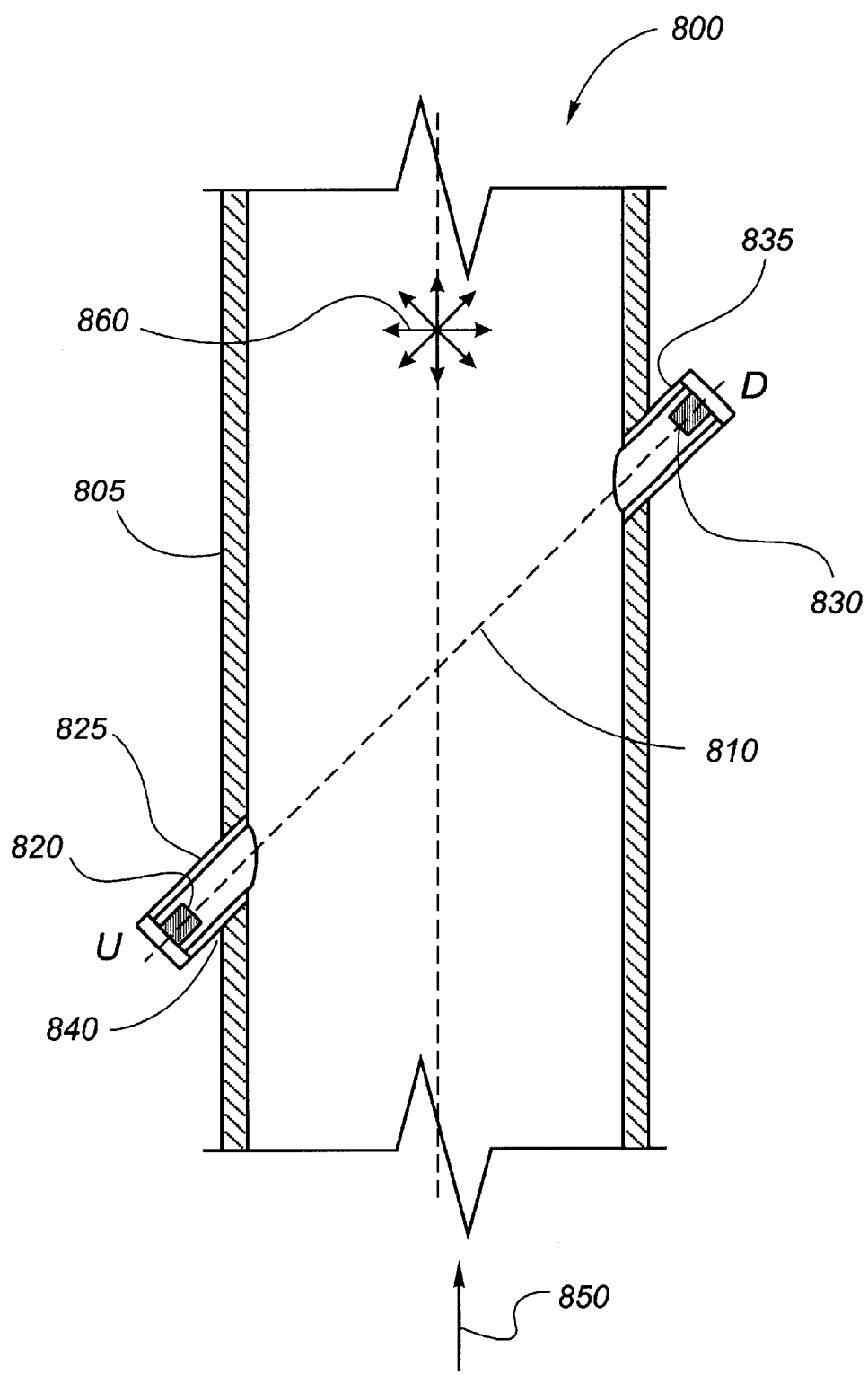
FIG. 8 is a cut-away profile view of an ultrasonic meter.

Referring to FIG. 8, ultrasonic meter 800 includes a spoolpiece body 805 having transducers 820 and 830 contained in transducer ports 825 and 835, respectively. These transducers 820 and 830 define a chord 810. As is readily appreciated, such an ultrasonic meter may have additional transducers or bounce paths. Also shown is a point of coupling 840 and a noise source 860. Gas travels downstream as indicated by arrow 850. In a dry gas stream, ultrasonic signals travel back and forth between the two transducers almost solely along chord 810. Because there is minimal coupling of the ultrasonic signal to the spoolpiece body 805, in a dry gas stream only a minimal portion of the ultrasonic signal uses the spoolpiece body 805 as a propagation medium. However, the introduction of fluid to the gas stream increases the coupling of an ultrasonic signal with the spoolpiece body 805. This coupling occurs at a variety of locations, such as point 840. Further, as more fluid is present in the gas flow, more coupling occurs between the ultrasonic signals and the spoolpiece body 805. This effect is significant because the spoolpiece body 805 of a meter typically has a faster speed of sound than does the speed of sound in gas. This results in a first portion of an ultrasonic signal arriving at a receiving transducer via the spoolpiece body 805 prior to the arrival of a major portion of the ultrasonic signal via chord 810. This first portion is identified as noise in FIGS. 9A–9D.

Referring now to FIG. 9, the level of noise arriving prior to the beginning of the main portions of the ultrasonic signals may be used to estimate the amount of fluid in a spoolpiece. FIGS. 9A and 9B show a first waveform 900, which represents the received upstream and downstream signal, respectively, corresponding to an ultrasonic signal that traveled through a dry gas stream in a 6" pipeline. A time before reception of the first waveform is generally labeled 910. A time after reception of the first waveform is generally labeled 915. As can be seen, there is minimal noise during the time 910 before reception of the ultrasonic signal. Waveform 900 has a signal-to-noise ratio of about 65,000 on the upstream side and about 5000 on the downstream side. The ER (energy ratio) of the signal is about ninety-one on the upstream side and about ninety-eight on the downstream side. Energy ratio is a measure of signal quality and its value is a by-product of the method taught in pending U.S. patent application "Measuring Time of Flight of a Signal," Ser. No. 08/964,577, a continuation of U.S. patent application Ser. No. 08/086,738, now abandoned. As such, the teachings therein are hereby incorporated by reference. More precisely, that document teaches a simple manner to find for a received waveform an energy ratio called $ER_n$, which is a moving average of the energy in a received waveform. The invention generally disclosed therein uses the time of a maximum $ER_n$ to determine the time for the beginning of a received signal. In contrast, the present invention uses variations in the amplitude of a measured maximum $ER_n$ to establish signal quality.

Figure 9A:
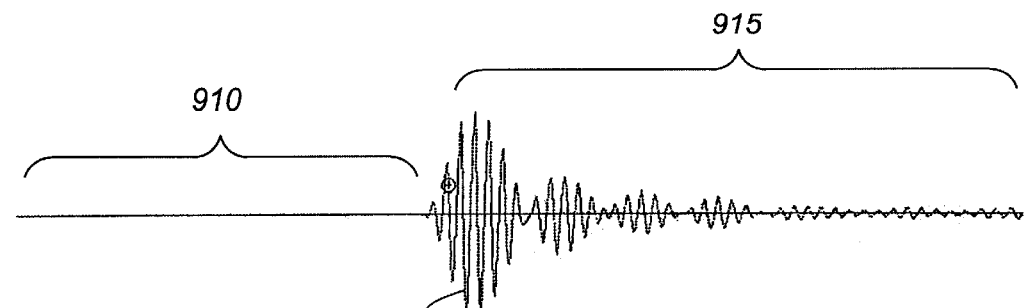
FIG. 9A is a received waveform on the upstream side of a 6" meter corresponding to an ultrasonic signal in a dry gas stream.
Figure 9B:
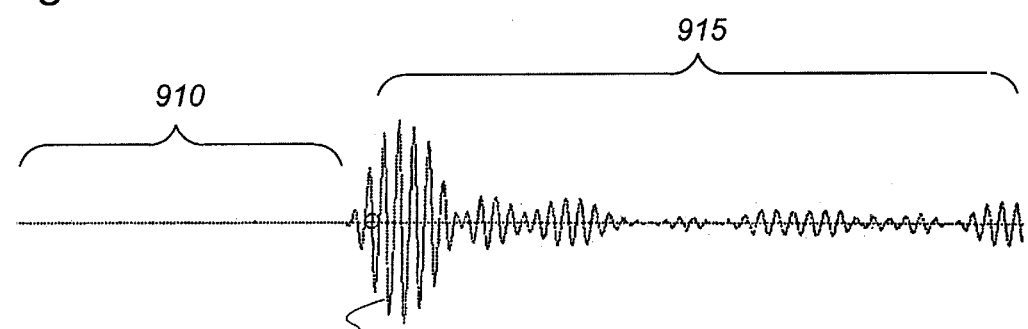
FIG. 9B is a received waveform on the downstream side of a 6" meter corresponding to an ultrasonic signal in a dry gas stream.
Figure 9C:
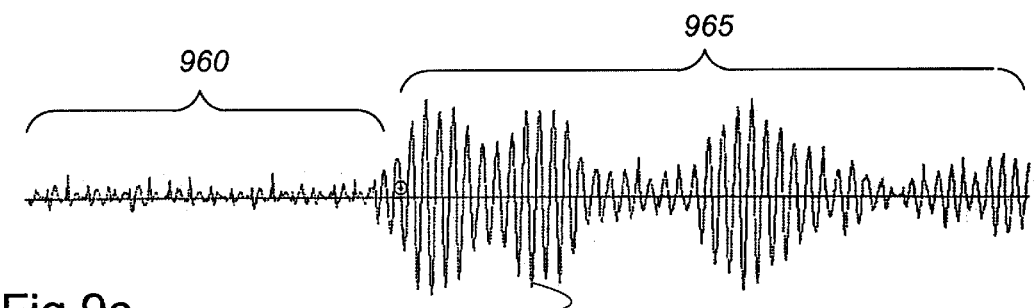
FIG. 9C is received waveform on the upstream side of a 6" meter corresponding to an ultrasonic signal in a gas stream including liquid.
Figure 9D:
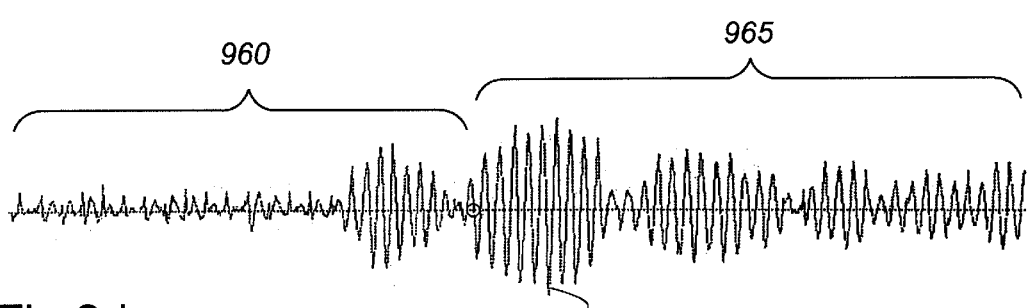
FIG. 9D is received waveform on the downstream side of a 6" meter corresponding to an ultrasonic signal in a gas stream including liquid.

FIGS. 9C and 9D show a second waveform 950, which represents the received upstream and downstream signal, respectively, corresponding to an ultrasonic signal that traveled through a wet gas stream in a 6" pipeline. A time before reception of the first waveform is generally labeled 960. A time after reception of the first waveform is generally labeled 965. Waveform 950 has a signal-to-noise ratio of about fifty-three on the upstream side and about forty-five on the downstream side. The ER of the signal is about seven on the upstream side and about nine on the downstream side. As can be seen, there is substantially more noise during the time 960 before reception of the ultrasonic signal than was present with respect to waveform 900. Further, substantially more noise is present during time 965 than was present with respect to time 915. As can also be appreciated, this increase in noise is reflected in the measured parameter S/N and ER. Hence, a measure of the signal quality of a received waveform, can indicate the Liquid Volume Fraction in the gas stream.

Figure 11:
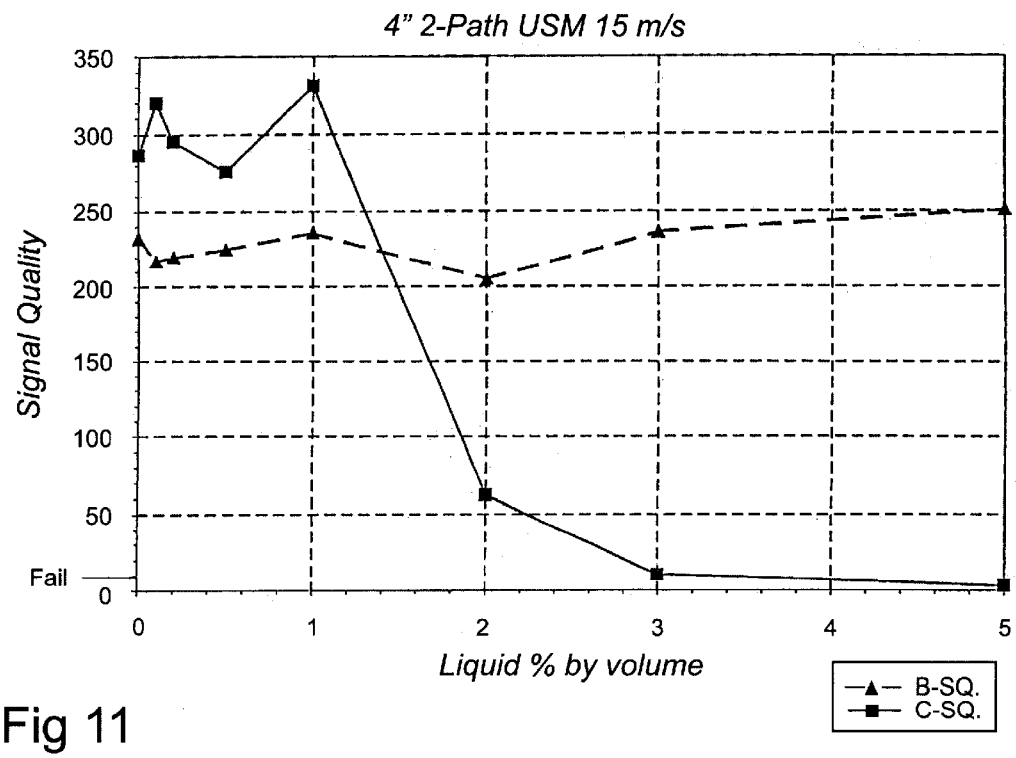
FIG. 11 is a graph illustrating a percent liquid fraction—signal quality relationship.

FIG. 11 depicts a Liquid Volume Fraction—signal quality relationship for a two-chord 100 mm ultrasonic meter. Along the X-axis is the liquid % by volume ranging from 0 to 5%. Along the Y-axis is signal quality measured from 0 to 350. A signal quality relationship for both chords B and C is shown. Chord B remains relatively constant and high in a range of about 200–230 across the liquid percentages shown. Chord C, however, shows significant deterioration at about 1% Liquid Volume Fraction.

However, signal quality alone is not an ideal criterion to measure the amount of liquid in the gas stream because, in addition to liquid in the gas stream, signal quality may be affected by other phenomenon. For example, a variation in signal quality may be due to one or more faulty transducers or may be due to pressure variations in the gas stream.

Figure 10:
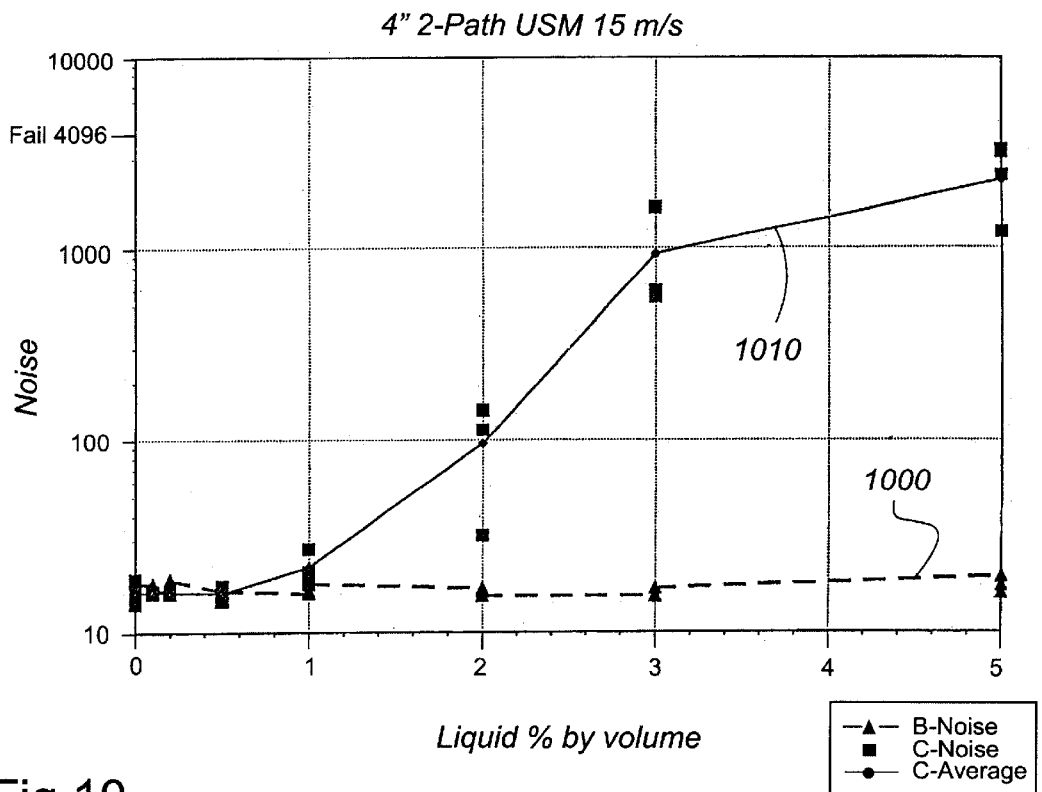
FIG. 10 is a graph illustrating a percent liquid fraction—noise relationship.

Similarly, FIG. 10 shows a percent liquid fraction—noise relationship from a 100 mm ultrasonic meter. Along the X-axis is percent liquid fraction by volume from 0% to 5%. Along the Y-axis is a logarithmic measure of noise from 10 to 10,000, with a defined failure level of 4096. Because of the small 100 mm size of the meter, only two chords are present and thus only chords B and C are depicted in FIG. 10. Data lines 1000 and 1010 are average value lines for the shown data points and loosely correspond to chords B and C as shown in FIG. 1B. As can be seen, the noise corresponding to chord-B data line 1000 remains relatively constant and low across the entire range of Liquid Volume Fraction. However, the noise corresponding to chord-C data line 1010 shows a definite increasing trend as more liquid is introduced into the gas stream. More particularly, FIG. 10 shows an increasing trend for data line 1010 as liquid fraction increases. This increase is attributable to scatter of the ultrasonic signals across the spoolpiece. The shown relationship would be expected to change somewhat with a different meter size. This parameter may be measured by monitoring the signal-to-noise ratio of the received ultrasonic signal. With automatic gain control, the signal amptitude is fixed, making noise and S/N ratio equivalent.

However, one drawback to using noise as an indicator of Liquid Volume Fraction in the gas stream is a multitude of other possible noise sources. Referring back to FIG. 8, noise source 860 is shown. Noise source 860 could be, for example, a valve. One manner to distinguish noise from increased coupling of the ultrasonic signal from the presence of noise due to some upstream or downstream source is by analysis between the upstream and downstream transducer (or transducers) of the received noise. As can be seen, because of its geometry, transducer 820 facing toward the noise source 860 is more likely to receive a strong noise signal than is transducer 830, which is facing away from the noise source 860. Such a dichotomy is much less likely when the presence of noise is due to liquid in the gas stream.

Yet another indicator of liquid in the gas stream is the failure rate of chords in the meter. In particular, for each ultrasonic signal, a variety of measurements are consistently taken. Each set of these measurements is called a "batch."

For example, a batch of various measurements is taught in the aforementioned U.S. patent application "Measuring Time of Flight of a Signal," Ser. No. 08/964,577, the teachings of which are hereby incorporated by reference. Each of the measurements in the batch (10–30) must fall within certain predetermined boundaries to be considered valid or legitimate. If any one of these measurements falls outside its predetermined boundaries, it is discarded. If more than a particular percentage of measurements in a batch fail, then the associated chord is classified as a failed chord. Although some degree of flexibility is possible, a forty-percent failure rate has been used to identify failed chords.

Figure 12:
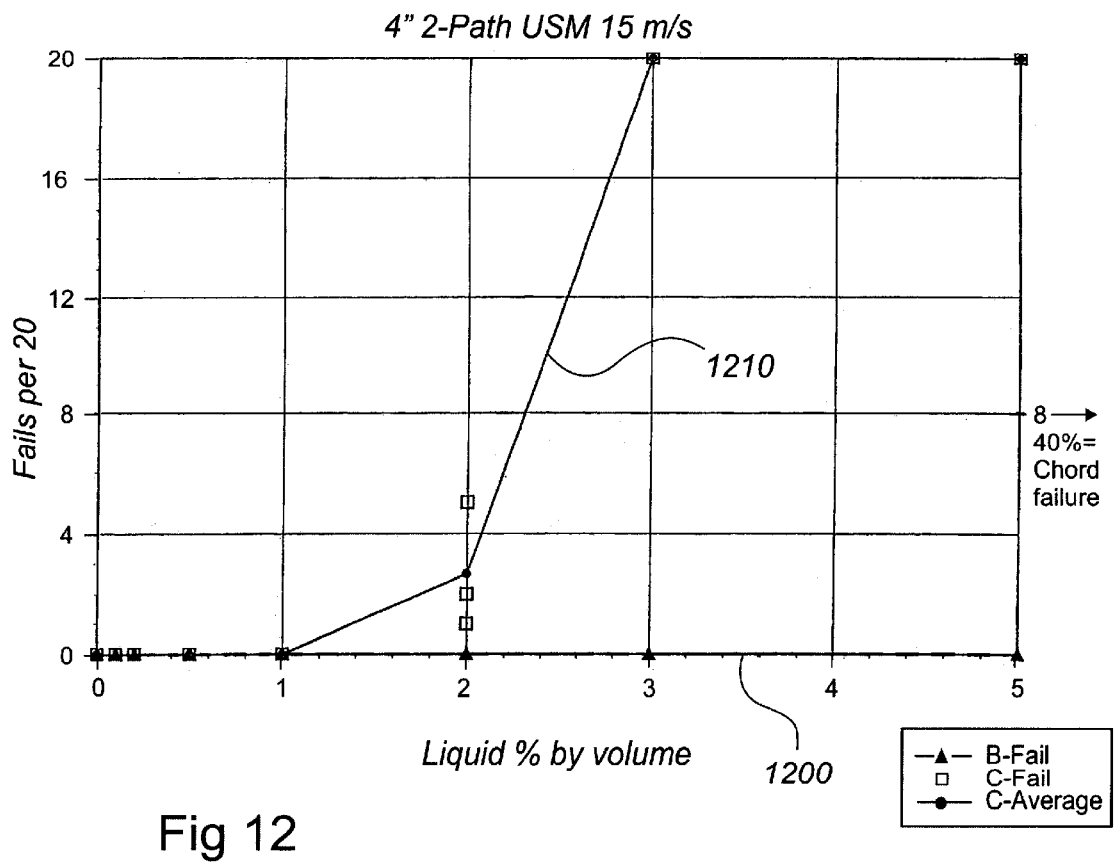
FIG. 12 is a graph illustrating a percent liquid fraction—batch failure rate relationship.

Failure rates have been found to be threshold indicators of the amount of liquid in the gas flow. FIG. 12 shows a liquid fraction—failure rate relationship for chords B and C on a 100 mm ultrasonic meter. Along the X-axis is the liquid % by volume ranging from 0% to 5%. Along the Y-axis is the failure rate measured from 0 to 20. Two data lines are shown, with each being the average value for the shown data points. Data line 1200 corresponds to chord B, whereas data line 1210 corresponds to chord C. As can be seen, the number of failures for chord B is zero all along the shown range of liquid percent by volume. Chord C, however, begins to show a significant rise in the number of failures at about 2% Liquid Volume Fraction. From about 2% liquid to about 3% liquid, failures rise from about 3 to 20. However, failures alone are not a reliable indicator of the amount of liquid in the gas stream because failures may also result from, for example, transducer failures.

It has also been found that the velocity profile of the gas flow can be used to infer the amount of fluid in the gas stream. For example, because the droplets that comprise a liquid mist have mass, any gas that carries them is slowed thereby. As explained above it is believed that gravity causes liquid in the form of a mist to be denser toward the bottom of a spoolpiece than toward the top. Thus, the gas toward the bottom of a spoolpiece travels more slowly than it would were it dry. Further, for any given average gas flow, the gas toward the top of the spoolpiece must travel faster than would its dry gas counterpart.

Figure 13:
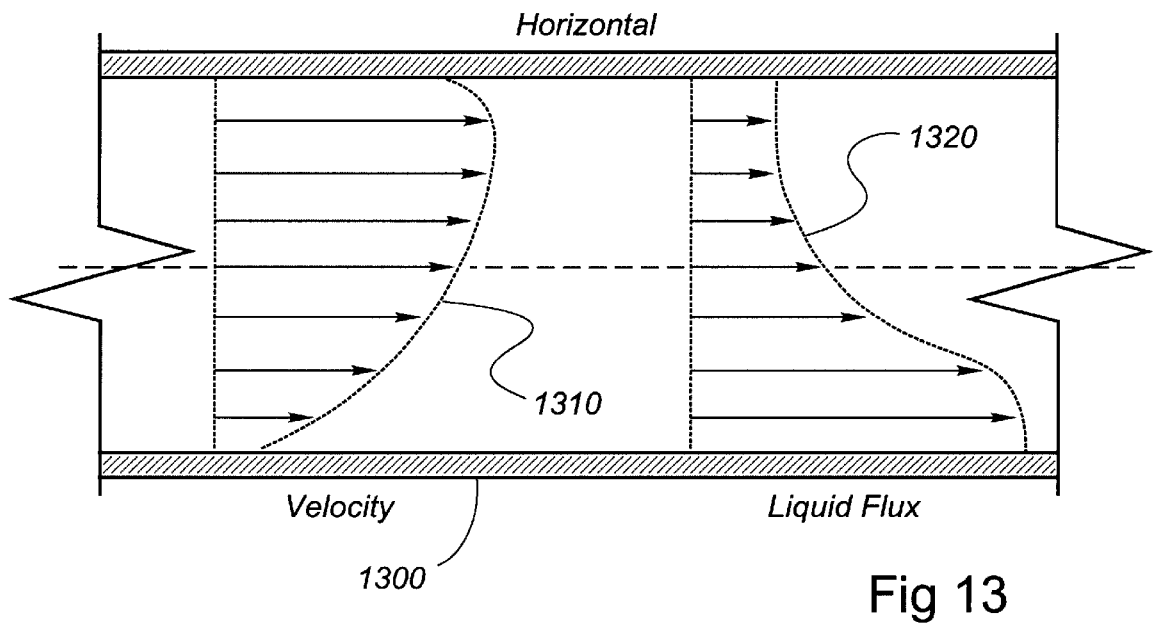
FIG. 13 is a side cut-away view of a spoolpiece showing an exaggerated velocity flow profile and liquid flux.

FIG. 13 shows an exaggerated example of a velocity profile altered from liquid present in the pipeline. A pipeline 1300 includes a velocity profile 1310 for a gas stream. As can be seen, this velocity profile is bowed from the presence of liquid in the gas stream. Also shown in FIG. 13 is an exaggerated liquid flux 1320. As can be seen, substantially more liquid is present at the bottom of the pipeline 1300.

Figure 14:
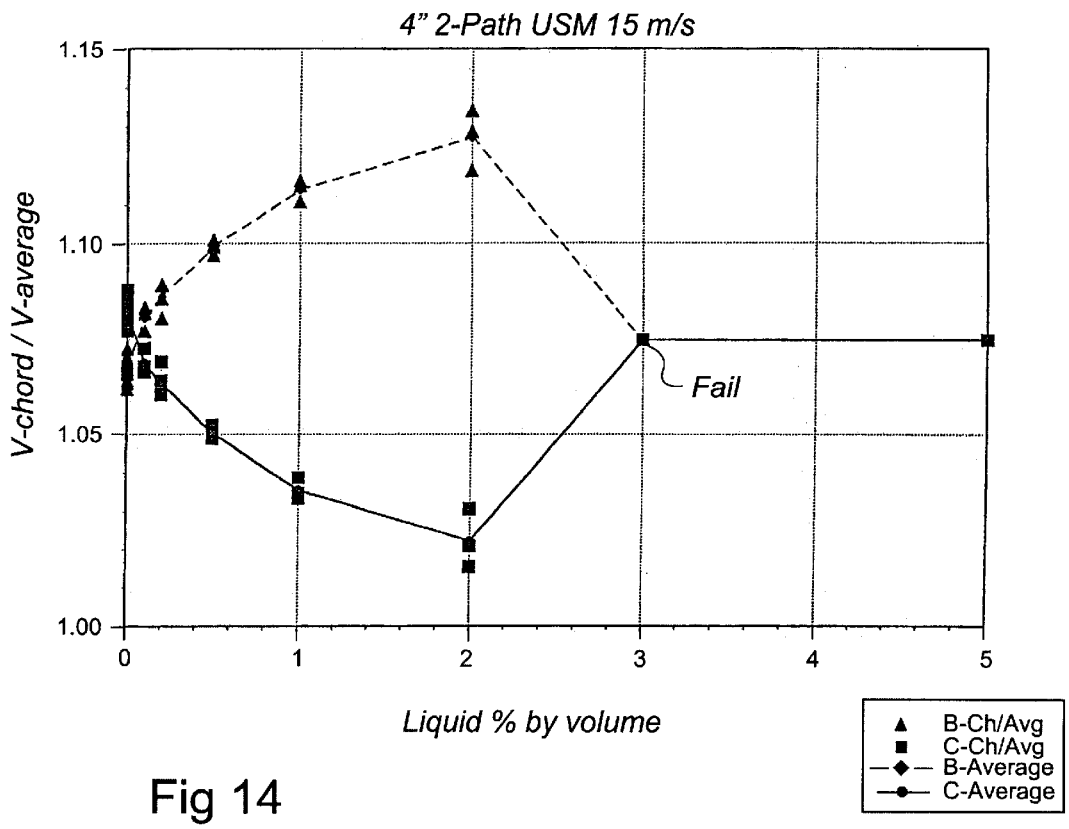
FIG. 14 is a graph illustrating a percent liquid fraction—chord velocity relationship.

FIG. 14 is a graph showing a percent liquid fraction—chord velocity relationship for chords B and C on a 100 mm ultrasonic meter. More particularly, along the X-axis is shown a range of percent liquid fractions by volume from 0% to 5%. Along the Y-axis is shown a ratio of chordal velocity to average velocity for the gas stream. The data lines shown correspond to the average of the depicted values for chords B and C with respect to the indicated ratio. At percent liquid fractions below about 2% the lower C chord shows a steadily decreasing trend as the percent liquid increases. Similarly, the upper B chord shows a steadily increasing trend to about 2% liquid in the gas stream. At some liquid percentage between 2% and 3%, chord C fails. The exact liquid percentage at which failure occurs is unclear because measurements were taken at two and three percent liquid.

Surprisingly, the velocity profile of a gas stream having a stratified flow is about the same as for the mist flow for any particular percent fraction of liquid. This is believed to be true because the gas flowing over the surface of the stratified flow is slowed by its interaction with the stratified flow. Similarly, gas carrying a mist flow of liquid is also slowed by its interaction with the mist flow. Hence, in either case, momentum is transferred from the gas to the liquid.

This observation may be used to make a determination whether a gas flow contains liquid in primarily a mist flow or primarily a stratified flow. Other parameters may be examined in combination with the velocity profile. If the velocity profile and the other parameters discussed above indicate that liquid is present in the gas stream, then it may be safely concluded that a primarily mist flow of liquid is present in the gas stream. If, on the other hand, the velocity profile indicates that liquid is present in the gas stream but the other parameters do not suggest this, then it may be concluded that a primarily stratified flow of liquid is present in the gas stream.

As can now be appreciated, the use of changes in measurements may yield a better indication of the amount of liquid in the gas stream than will use of absolute measurements. Stored historical data can be used to confirm the properties of a two-phase flow. Further, any one of the disclosed parameters may be used alone or in combination with one or more of the other disclosed parameters. The greater the number of parameters used, the higher the confidence the user may have in the indication of Liquid Volume Fraction. In addition, the teachings herein are not limited to the disclosed ultrasonic meters, but instead may be used with any meter making the disclosed measurements.

As can be appreciated, use of many parameters to give reliable measurements of percent liquid fraction can result in a large database of calibration parameters. For example, the parameters gain, velocity of sound (VoS), standard deviations, and failure rates all show smooth changes as liquid condensate is added to the gas and can be well fitted by second order polynomials. However, four chords with three measurement methods (e.g. gain, VoS, standard deviations), each requiring three coefficients for a quadratic fit, requires thirty-six (3×4×3) coefficients, each of which will vary with conditions. Thus, a method or methods to reduce the number of variables needed to fit the data is desirable. The method or methods also should be consistent with the physics of two-phase flow.

The first step is to normalize all data to the A chord, which remains almost free of liquid when the meter is close to horizontal. This normalization removes effects such as variations in gas pressure and density, despite the fact that these parameters are not yet known. The data may then be analyzed in two ways: 1) method 1—used when all four chords are working, approximately 1% liquid by volume; or 2) method 2—used when at least one chord has failed. Regardless, the following terms are used:

Liquid Flux F=liquid volume as a percent of unit volume in relevant part of the pipe, $F_i$=average liquid flux in the ultrasonic path of chord i, Liquid % L=total volume as a percent of the total pipe volume, $L_i$=total liquid volume in the pipe 'quadrant' represented by chord i, expressed as a percent of the total pipe volume.

For example, if the pipe contains 5% liquid by volume, then L=5%. Typically, the amount of liquid in each quadrant may be $L_d$=4%, $L_c$=1%, $L_b$=$L_a$=0. (The $L_i$ must always sum to L). But the average liquid flux in the D quadrant may be 20%, i.e., the liquid flux at the bottom of the pipe is much greater than the 5% average.

The first method, method 1, requires that for each type of measurement (e.g., gain), a "Measured parameter" $M_i$ (i=a, b,c,d) is identified which is assumed to be directly proportional to the amount of liquid "seen" by the corresponding chord. In the case of gain, the measured parameter is the gain difference between wet gas and dry gas at the same conditions. Because gain is logarithmic, the gain difference is a measure of the ratio of signal strength. For the B chord, this is:

$$M_b=(GAIN_b-GAIN_a)-OFFSET_b \quad (1)$$

Where OFFSET is a fixed value accounting for differences in transducers and chosen so that for dry gas, $M_b$=0.

For the velocity of sound and standard deviations, the $M_i$ are the differences from the A chord expressed as a percentage of the A chord, so that for example:

$$M_d=100(VoS_a-VoS_d)/VoS_a \quad (2)$$

Where VoS is the velocity of sound. Given sets of measurements of $M_i$ and associated values of total injected liquid, the meter should be calibrated for liquid and should measure liquid percent values with acceptable accuracy under all operating conditions. To accomplish this, it is assumed that the measured parameters give a direct (linear) measurement of the liquid in the path of the ultrasonic beams between the pairs of transducers, such that:

$$F_i=C*M_i \quad (3)$$

Where C is a constant calibration value, C that converts a measurement (e.g., change in gain) into a percent liquid flux C is the same for all chords and all conditions but changes for each parameter. As such, a single value of C will exist for gain, a different value of C will exist for VoS, etc. However, it is thought that this assumption is not entirely accurate and C may vary, roughly in proportion to flow velocity, at least in the case of VoS.

Figure 1C:
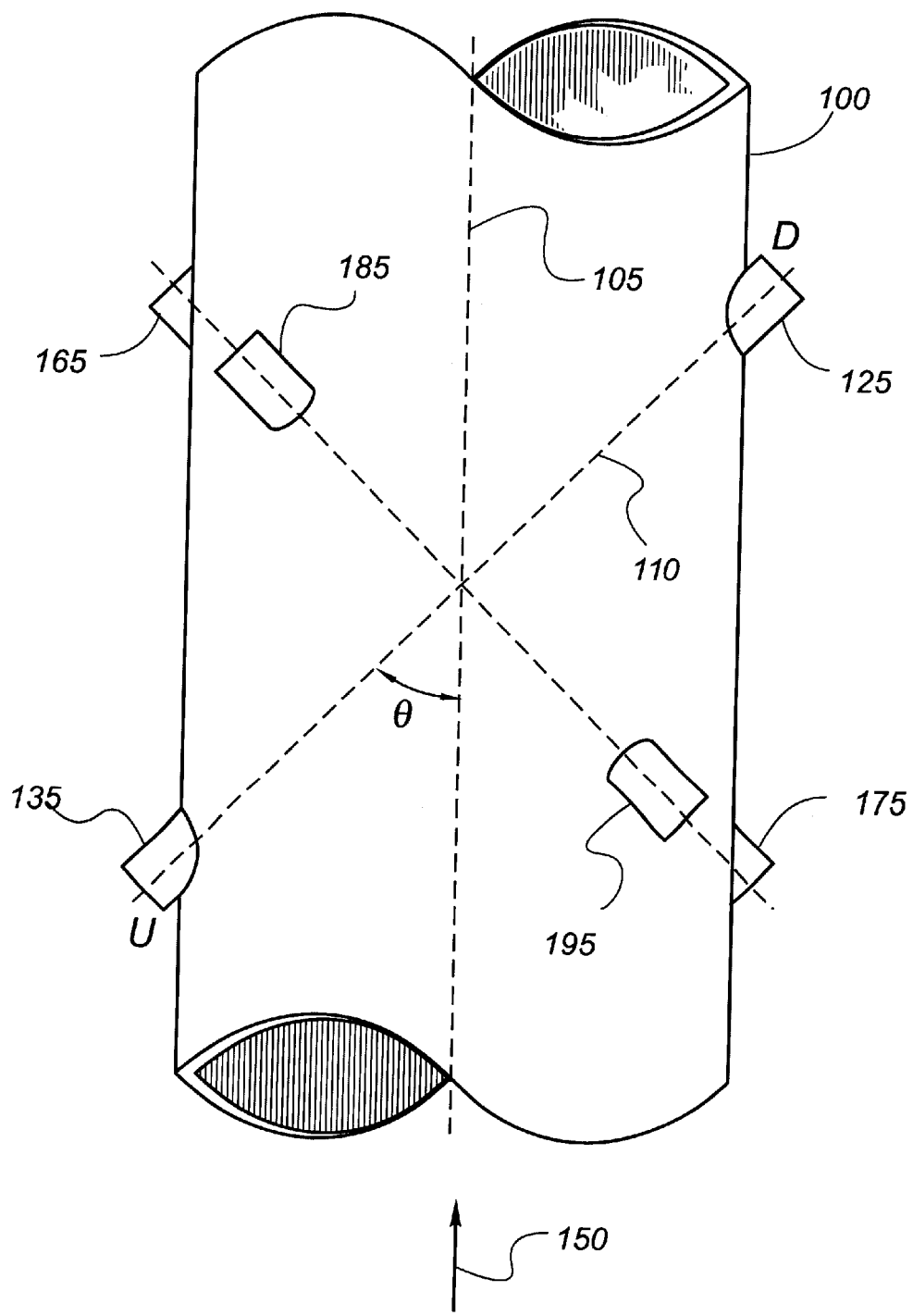
FIG. 1C is a top view of a spoolpiece housing transducer pairs.

Weighting factors should also be established. The weighting factors $W_i$ should be defined as the fraction of the total volume of the spoolpiece represented by each chord. Thus, for example, with a four chord meter as shown in FIG. 1, the weighting factors are the same as used in the ultrasonic flow calculations (i.e., $W_a$, $W_b$, $W_c$, $W_d$=0.14, 0.36, 0.36, 0.14).

A second assumption applied with method 1 only is that the total liquid in a quadrant is the liquid flux seen by the ultrasonic beam, multiplied by the volume of the quadrant. As such, method 1 assumes that the liquid is fairly evenly dispersed across each quadrant so that the liquid flux seen by the chord is a good representation of the whole quadrant. This assumption means that the amount of liquid in each section is:

$$L_i=W_i*F_i \quad (4)$$

This assumption also means that method 1 is independent of flow profile providing that the flow profile is not changing rapidly within a "quarter pipe," as happens with stratified flow. In addition, when the liquid is stratified, or almost stratified, this assumption fails because most of the liquid will lie below the D chord and will not be detected.

In the case of gain and standard deviations, these weighting factors are adjusted to take into account the fact that the two middle chords are approximately 1.6 times longer than the outer chords, and will, therefore, show a larger effect. This gives effective weighting factors of approximately 0.2, 0.3, 0.3, and 0.2.

The total liquid is $$L = \Sigma L_i \quad \text{volume \%}$$
$$= \Sigma W_i * F_i$$
$$= C \Sigma W_i * M_i \quad (5)$$

C can be measured from empirical data, and then used to recalculate L, the percent total liquid.

The second method for calculating percent liquid fraction, method 2, essentially calibrates each chord individually, and so can be used when one or more chords have failed. A first step of this second method is to define "Profile Factors," $P_i$, such that $$P_i = F_i / L. \quad (6)$$

So that, $$L = F_i / P_i = C * M_i / P_i. \quad (7)$$

This results in $P_i$ being the ratio of the local liquid flux seen across chord i to the total injected liquid. Thus, each chord may be calibrated at different conditions by measuring $P_i$:

$$P_i = C * M_i / L \quad (8)$$

We can then use these values to calculate $L = CM/P_i$.

Method 2 does not make any assumptions about flow profile, but relies on an accurate set of data supplying the profile factors $P_i$ at the measurement conditions. The $P_i$ factors will vary with the measured value $M_i$, gas flow velocity, pressure, temperature, composition of the measured gas, and metersize.

This approach splits the problem into two parts—the C factors are a measure of the instrument's response to liquid and should be constant for each type of measurement (e.g. gain). The profile factors are a measure of the vertical liquid distribution—they will vary with conditions, but should be the same for all methods of measurement, e.g., gain and VoS should give the same results.

It has been found that the second method shows a good straight line fit between profile factors and total liquid percent. The profile factors for chords A, B, and C were found to increase in proportion to the total injected liquid. This effectively means that the local liquid flux on these chords increases with the square of the injected liquid (if the total liquid is increased by a factor of two, the liquid on all chords increases by a factor of two, but the fraction of liquid moved up from the D chord to the higher chords also increases by a factor of two).

Because the total liquid in the pipe must sum to the known total, the profile factors for the D chord could be calculated from the A, B, and C chords and was found to be in reasonable agreement with the (widely scattered) measurements on the D chord. Calculations of the total liquid percent can be made from the raw data on each individual chord using only four "calibration constants" overall including the C factor derived from method 1 and the three slops of the straight lines connecting profile factor to liquid percent L for chords A, B, C.

It has been found that method 2 gives a good fit to the gain data on all chords using only five "variables," i.e., calibration factor C and the four constants relating the profile factors $P_i$ to total liquid percent. However, the profile factors are not as accurate as desirable with respect to VoS.

Further, it has been found that all chords fail when the local liquid flux reaches approximately 4.5%. The usable ranges of the four chords are:

Chord D or Method 1: 0 . . . 1%
Chord C: 0.7 . . . 3%
Chord B: 1.7 . . . 7.5%
Chord A: above 4%

This gives a good overlap, but above about 7.5% liquid, a loss of accuracy occurs as normalization may no longer be made to the A chord (the only remaining chord still operating). Possible operating boundaries include a flow velocity from 5 m/sec to 20 m/sec (poor accuracy below 5 m/sec due to stratification), liquid % by volume 0% to 7.5%, with reduced accuracy above 7.5%, and a repeatability of ±0.06% liquid volume over the range. The absolute accuracy depends on the accuracy with which the C and $P_i$ factors can be determined at different conditions.

Use of parameters such as gain, VoS, etc. to determine percent liquid in the two-phase flow is advantageous because those parameters are already determined for other purposes by known ultrasonic flow meters. Nonetheless, if solely a liquid fraction measurement device is desired, other embodiments are possible. Alternately, a liquid fraction measurement device may be combined with an ultrasonic flow meter to improve its performance.

Figure 15:
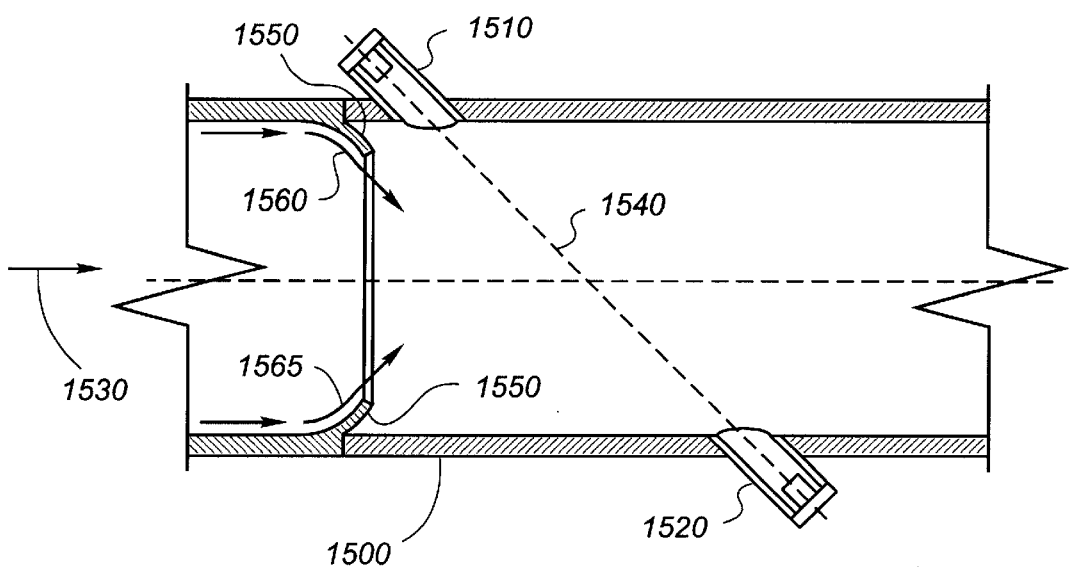
FIG. 15 is a side cut-away view of a spoolpiece including a lip.

Referring now to FIG. 15, a spoolpiece or pipeline 1500 carries a gas stream flowing in a direction indicated by arrow 1530. At least one pair of transducer ports 1510 and 1520 correspond to chord 1540. Inside pipeline 1500, a lip 1550 is placed upstream of the transducers contained in transducer ports 1510 and 1520. This lip 1550 provides a mechanism to change a stratified flow of liquid 1560, 1565 to a mist flow. Liquid traveling in a stratified flow along the periphery of the spoolpiece or pipeline 1500 will be propelled by lip 1550 toward the center of the spoolpiece or pipeline 1500. This projection should result in a temporary mist flow. As can be appreciated, for a near-horizontal spoolpiece where the stratified flow occupies only the bottom of the spoolpiece, such a lip 1500 may travel only a portion of the way around the spoolpiece.

Because the characteristics of a mist flow may be determined with more precision than a stratified flow, such a lip can increase the accuracy of a measurement for transducers in ports 1510 and 1520. Such an approach would be especially effective at higher mean flow velocities and would help reduce the velocity needed to establish mist flow. However, lip 1550 is not ideal when the transducers are being used as part of an ultrasonic meter because the lip 1550 changes the flow profile in the pipeline or spoolpiece. As such, the flow profile would no longer approximate the ideal as shown in FIG. 1A. In part because the calibration factors used by an ultrasonic meter were determined for a velocity profile generally as shown in FIG. 1A, lip 1550 would introduce error into measurements made by the ultrasonic meter. However, this error is not severe for a multi-path meter.

Figure 16:
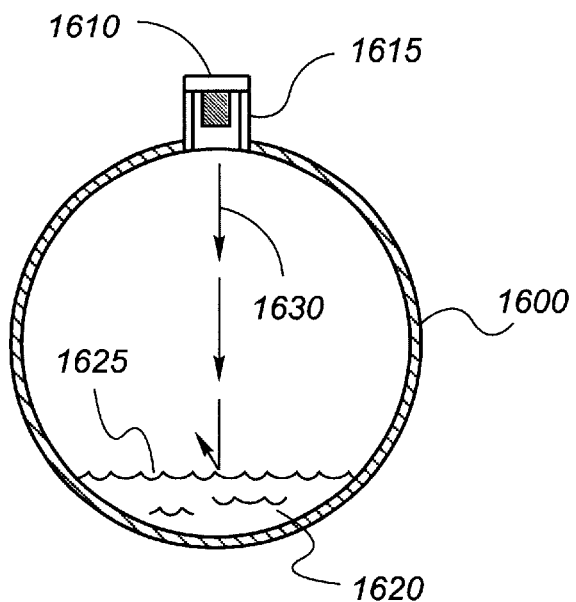
FIG. 16 is a first single transducer embodiment of the present invention.

FIG. 16 shows a single transducer embodiment to determine the level of stratified flow in a pipeline or spoolpiece. Transducer 1610 is connected to of spoolpiece 1600 by port 1615. For a near-horizontal spoolpiece, transducer 1610 is at the top of the spoolpiece, as shown. Spoolpiece 1600 also caries a stratified flow 1620 of liquid with a surface 1625. Transducer 1610 generates a signal 1630 that travels across the spoolpiece 1600, reflects off of the surface 1625 of stratified flow 1620, and returns to transducer 1610. Thus, the travel time of ultrasonic signal 1630 corresponds to the depth of stratified flow 1620. Given the dimensions of spoolpiece or pipeline 1600, the amount of liquid traveling in a stratified flow may then be determined.

Figure 17:
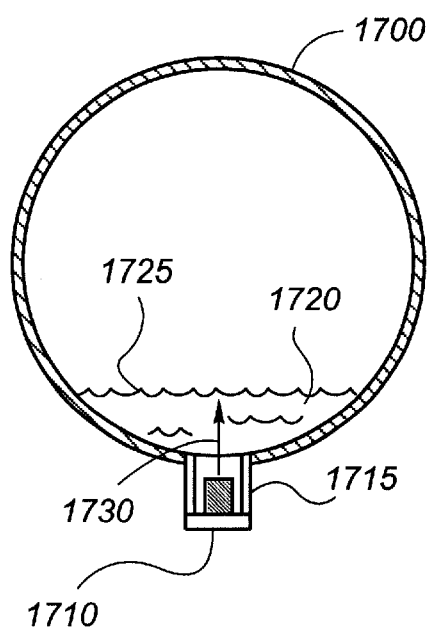
FIG. 17 is a second single transducer embodiment of the present invention.
Figure 18:
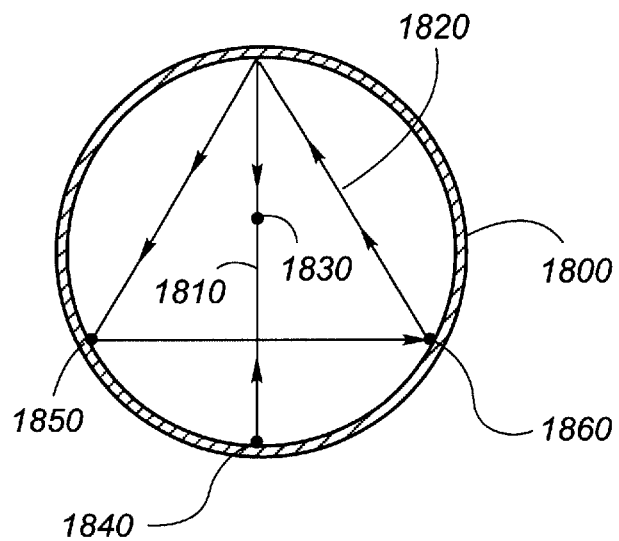
FIG. 18 is an end view of a bounce path ultrasonic flow meter.
Figure 19:
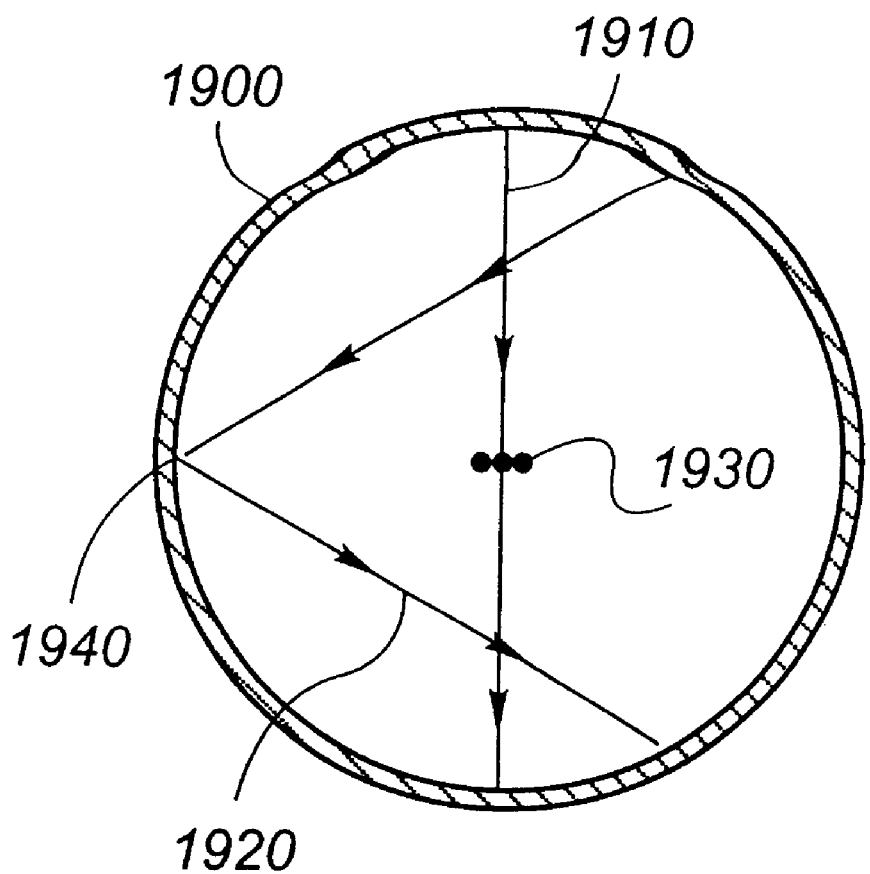
FIG. 19 is an end view of a second bounce path ultrasonic flow meter.

FIG. 17 shows an alternate embodiment to that shown in FIG. 16. A transducer 1710 is coupled to spoolpiece 1700.

A stratified flow of liquid 1720 including surface 1725 resides in the bottom of spoolpiece 1700. Transducer 1710 couples to the exterior of spoolpiece 1700 by port 1715. A signal 1730 generated by transducer 1710 travels through the stratified flow 1720 before reflecting from the surface 1725 of stratified flow 1720 and returning to transducer 1710. The time between generation of reception of ultrasonic signal 1730 may be used to determine the depth of stratified flow 1720. Like the embodiment of FIG. 16, the level measurement device of FIG. 17 employs a single transducer to determine the level of stratified flow in a pipeline or spoolpiece. However, unlike the embodiment of FIG. 16, the measurement device of FIG. 17 couples to the bottom of spoolpiece or pipeline 1700.

The arrangement of FIG. 1 can also be used as a cut-off switch to determine stratified flow level. Upon the stratified flow reaching about 5% of the total volume of the spoolpiece, it occupies the space used by chord D. As such, chord D ceases to operate and stops providing information transmitted and received ultrasonic signals.

Upon understanding of the teachings above, a processor or computer may be programmed to estimate accurately the amount of liquid in a gas stream. It may also be programmed to estimate accurately the individual flow rates of the liquid and the gas, or it may accomplish both. This processor may be part of an ultrasonic meter or may be separate.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. An apparatus suitable for measurement of the properties of a two-phase flow of liquid and gas, comprising:

means for measuring a parameter with respect to said gas; and means programmable for estimating based on said parameter a fraction of said liquid in said gas and a flow rate for either of said liquid and said gas.

2. A meter to determine the percentage of a liquid present in a volume of gas, the meter comprising:

a first transmitter suitable to transmit ultrasonic energy through said volume of gas;

a detector positioned to receive said ultrasonic energy and further configured to detect said ultrasonic energy; and a processor associated with said detector, said processor programmed to analyze at least one parameter of said ultrasonic energy to determine one or more variations, said one or more variations corresponding to said percentage of liquid present in said volume of gas.

3. The meter of claim 2, wherein said processor determines a function such that at least one of said one or more variations correspond to and are a function of changes in gain of instrumentation associated with said ultrasonic energy received at said detector.

4. The meter of claim 2, wherein said first transmitter, said detector, and said processor are all part of an ultrasonic flow meter.

5. The meter of claim 2, wherein said processor analyzes said at least one parameter to evaluate at least one of mist flow characteristics and stratified flow characteristics associated with said liquid fraction such that said characteristics are a function of the liquid fraction in the volume of gas.

6. The meter of claim 2, wherein said ultrasonic energy is an acoustic signal above approximately 20,000 hertz.

7. The meter of claim 2, wherein said detector is a transducer that generates an electrical signal, said electrical signal being transmitted to said processor.

8. The meter of claim 2, wherein said at least one parameter includes attenuation of the ultrasonic energy.

9. The meter of claim 2, wherein said at least one parameter includes a standard deviation of travel time differences associated with said ultrasonic energy.

10. The meter of claim 2, wherein said at least one parameter includes a velocity of sound.

11. The meter of claim 2, wherein said at least one parameter includes stratified flow characteristics.

12. The meter of claim 2, wherein said at least one parameter includes mist flow characteristics.

13. The meter of claim 2, wherein said one or more variations are determined over a range of liquid fractions.

14. The meter of claim 2, wherein said at least one parameter includes noise.

15. The meter of claim 14, wherein said noise arrives at said detector prior to the majority of said ultrasonic energy.

16. The meter of claim 2, wherein said one or more variations include signal quality.

17. The meter of claim 16, wherein said signal quality is established based on the energy rate of change of said received ultrasonic energy.

18. The meter of claim 2, wherein said one or more variations include batch failure.

19. The meter of claim 2, wherein said meter further comprises:

a second transmitter to transmit ultrasonic energy through said volume of gas; and a second receiver to receive said ultrasonic energy from said second transmitter;

wherein said processor analyzes said at least one parameter corresponding to said ultrasonic energy from said first transmitter and corresponding to said ultrasonic energy from said second transmitter to establish a gradient across said volume of gas, said at least one parameter including said gradient.

20. The meter of claim 2, wherein said at least one parameter includes a velocity profile of said volume of gas.

* * * * *